US006449035B1

(12) United States Patent
Batchelder

(10) Patent No.: US 6,449,035 B1
(45) Date of Patent: Sep. 10, 2002

(54) METHOD AND APPARATUS FOR SURFACE PARTICLE DETECTION

(76) Inventor: John Samuel Batchelder, 2 Campbell Dr., Somers, NY (US) 10589

( * ) Notice: Subject to any disclaimer, the term of this patent is extended or adjusted under 35 U.S.C. 154(b) by 0 days.

(21) Appl. No.: 09/310,491

(22) Filed: May 12, 1999

(51) Int. Cl.[7] .............................................. G01N 21/00
(52) U.S. Cl. ............................... 356/237.1; 356/237.3; 356/238.3; 399/176; 399/101; 399/24
(58) Field of Search ........................... 356/237.1, 237.2, 356/237.3, 237.4, 237.5, 237.6, 238.3, 336, 337, 338; 250/574, 575, 559.46, 564; 399/101, 24, 176; 361/234

(56) References Cited

U.S. PATENT DOCUMENTS

| 4,009,047 A | * | 2/1977 | Lindsay ........................ 134/9 |
| 4,705,388 A | * | 11/1987 | Huntjens et al. .............. 399/24 |
| 4,766,324 A | | 8/1988 | Saadat ......................... 250/563 |
| 5,253,538 A | | 10/1993 | Swick ..................... 73/864.34 |
| 5,255,089 A | * | 10/1993 | Dybas et al. ............... 356/337 |
| 5,671,119 A | * | 9/1997 | Huang et al. ................ 361/234 |
| 6,023,597 A | * | 2/2000 | Mayuzumi et al. .......... 399/176 |

FOREIGN PATENT DOCUMENTS

WO    WO 93/20950    * 10/1993

* cited by examiner

*Primary Examiner*—Frank G. Font
*Assistant Examiner*—Sang H. Nguyen

(57) ABSTRACT

A method and an apparatus are described for detecting particles on surfaces. Particles are transferred from the surface to be inspected onto a tacky sheet by applying the tacky sheet to the surface and then removing the tacky sheet from the surface. Particles and defects are optically detected on the removed tacky sheet to produce location data. The tacky sheet is selected to leave no residue on the surface to be inspected. The tacky sheet is selected to be compatible with darkfield optical techniques. In one embodiment the tacky sheet is inspected prior applying the tacky sheet to the surface to be inspected, so that particles from the surface are identified as differences between the location data before and after applying the tacky sheet to the surface to be inspected. In one embodiment the tacky sheet is re-applied and reinspected many times before it is replaced.

14 Claims, 13 Drawing Sheets

FIG.5a-A   FIG.5a-B

METHOD AND APPARATUS FOR SURFACE PARTICLE DETECTION

BACKGROUND

Semiconductor chips are manufactured in conditions of extraordinary cleanliness to minimize process-induced defects. Technologies have been developed for inspecting the semiconductor wafers for particles and pattern defects, such as those described in U.S. Pat. Nos. 5,343,290, 5,317,380, 4,766,324, and 4,898,471. Inspection technologies have also been developed for analyzing the particulate content of the fluids in which the wafers get immersed, such as those described in U.S. Pat. Nos. 5,671,046, 5,067,814, and 5,061,070.

The surfaces of the process tools and wafer containers can also provide sources of particulates that can be transferred to wafers. Inspecting these surfaces is difficult for several reasons:
1. These surfaces are typically large and non-planar, making them incompatible with existing wafer scanners.
2. These surfaces often have random roughness that is large compared to the particle sizes of interest; this makes identifying particles against the rough background a difficult optical inspection problem.
3. The optical characteristics of the surfaces to be inspected vary from highly reflective to highly absorbing.
4. Non-optical inspection techniques for particles on surfaces, such as thermal emission and electron microscopy, are relatively slower scanning rate and bulkier in size than optical inspection techniques.
5. The time between inspecting the surface and determining the particle concentration should be short so that decisions can be made as to whether to clean the surface or put it in service.
6. Some of the most critical surfaces to be inspected, like the inside of a wafer box or a process tool, constrain the inspection apparatus to be a small size.
7. Particle detectors for this application have to have consistent and verifiable sensitivities to achieve repeatable process control.
8. Particle detectors should provide a data trail so that ancillary analysis equipment can determine the composition and nature of the particles.

A traditional method for inspecting process tool and wafer container surfaces for particles is to wipe the surface with a white cloth and visually check the cloth for discoloration. This technique is not sensitive to small particles and it is not quantitative.

Another method is useful for the surfaces of smaller objects. The object is placed in an ultrasonic cleaning bath for a period of time, and then the particulate concentration in the liquid in the ultrasonic cleaner is measured. This technique is time consuming, and generates data that does not consistently correlate with the particulate surface concentrations of the object.

Another method is described in U.S. Pat. No. 5,253,538 and is embodied in the product QIII® from Dryden Engineering. In this method clean air is passed across a surface using a nozzle assembly, and that air is then passed through an airborne particle counter. The surface to be inspected must be flat for this technique to be applicable.

SUMMARY

A method and an apparatus are described for detecting particles on surfaces. Particles are transferred from the surface to be inspected onto a tacky sheet by applying the tacky sheet to the surface and then removing the tacky sheet from the surface. Particles and defects are optically detected on the removed tacky sheet to produce location data. The tacky sheet is selected to leave no residue on the surface to be inspected. The tacky sheet is selected to be compatible with darkfield optical techniques. In one embodiment the tacky sheet is inspected prior applying the tacky sheet to the surface to be inspected, so that particles from the surface are identified as differences between the location data before and after applying the tacky sheet to the surface to be inspected. In one embodiment the tacky sheet is re-applied and re-inspected many times before it is replaced.

An object of this invention is to allow particulate inspection of non-planar surfaces.

Another object of this invention is to allow detected particles to be further analyzed by other inspection techniques.

Another object of this invention is to provide an apparatus that is portable and compact enough to be able to inspect the inside surfaces of semiconductor process tools.

BRIEF DESCRIPTION OF FIGURES

FIG. 5a shows two views of a roller with a tacky surface on a motor drive with an encoder.

DETAILED DESCRIPTION

Particles

Figure 1:
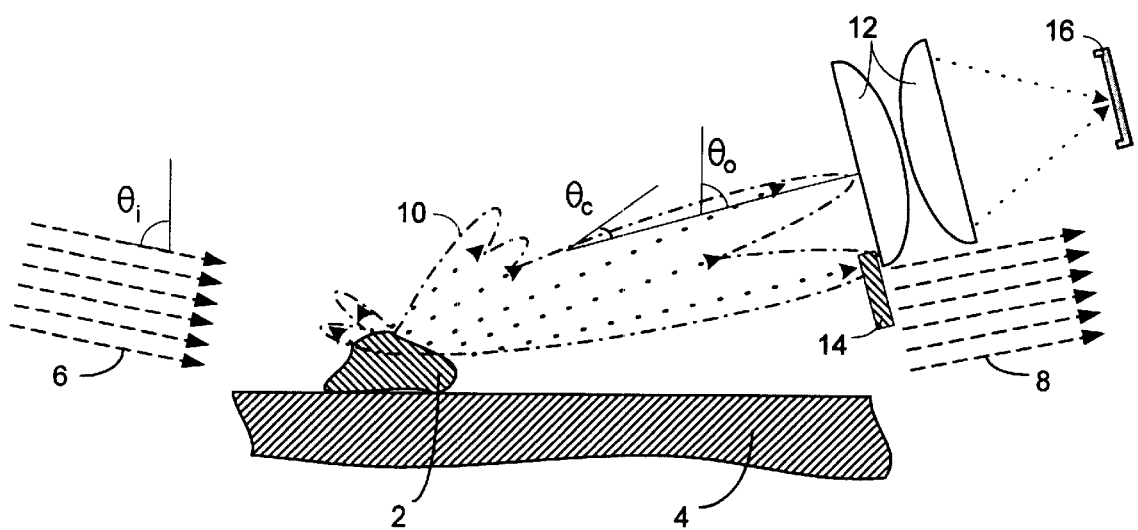
FIG. 1 shows light scatter from a particle on a surface due to grazing angle illumination.

Particles on the surfaces of tools and containers can impact yields in semiconductor manufacturing if the particles have a reasonable probability of being released and transported to the wafer. It is desirable not to count particles that are tightly bound to the inner surface of a process tool or wafer container, even though they may be large. Particles include mechanically rigid objects as well as gels, filaments, flakes, and droplets. Particles can have a wide range of optical absorption coefficients and indices of refraction.

Particles in air are considered large for light scattering if their mean circumference times their index of refraction is large compared to the wavelength of light. The details of how large particles scatter light is complex, however generally they extract optical power from the incident light corresponding to roughly twice their geometric cross section, and the light that they scatter is strongly biased in the forward scattering direction. Particles are considered small for light scattering if their mean circumference times their index of refraction is small compared to the wavelength of light. Small particles generally follow the Rayleigh light scattering model, and produce more isotropic scatter patterns.

Tacky sheets

Sticky or tacky surfaces are used for particle removal in many applications. The entrance of a typical clean room has a floor mat with an adhesive surface to reduce particles brought in on shoes. The adhesive in such a product called the M6090 Tacky Mat from Nano Times is about 3 mils thick with a peel strength of about 300 grams per inch. The Clean Roller from Alma Inc. is a foam cylinder covered with a film coated with a non-transferring adhesive. Katsura Roller Manufacturing Company manufactures rollers coated with a soft rubber for removing particles and other contamination from film, circuit boards, and ceramics. U.S. Pat. No. 4,009,047 describes a tacky roller apparatus for cleaning surfaces, including additional adhesive sheets to rejuvenate the tacky rollers. U.S. Pat. No. 4,705,388 describes a tacky roller for removing particulates implemented with an optical detector for determining the particulate loading on the tacky roller. U.S. Pat. No. 4,705,388 determines an average light reflectivity of the tacky roller; it does not teach detection of the locations of individual particles on the tacky roller.

A tacky sheet typically has an adhesive or high surface tension layer doctored or cast onto the surface of the sheet. A tacky sheet can have several geometric forms, including tape, a mobius strip, a disk, the surface of a conic section, the surface of an ellipsoid, and the surface of a cuboid. The surface of the tacky sheet can be perforated to allow for tractor feeding. A tacky sheet can be a cylinder with an adhesive or high surface tension layer applied to the cylinder directly, or it can be a cylinder wrapped with a prepared tacky sheet. Alternatively the adhesive or high surface tension layer can be sprayed, doctored, cast, or spun onto a cylinder or film.

A tacky sheet should have a relatively low concentration of particulates and defects on its surface when the tacky sheet is first put into service. Defects include all irregularities of the tacky sheet that cause light scattering events that imitate particles. Types of tacky sheet defects include pits, mounts, scratches, buried gels and particles,-and localized variations in index of refraction. If the tacky sheet is adhered to a surface once and inspected once and then is replaced, it is necessary for the tacky sheet to have a substantially smaller concentration of particulates and defects than the expected contamination levels on the surfaces to be inspected. If the tacky sheet is re-inspected after each cycle of adhesion and peeling, the total area of the tacky sheet in the proximity of the accumulation of particulates and defects must be no more than a few percent of the total area of the tacky sheet.

It is important that the tacky surface not leave residues as it is removed from the surface to be inspected. Such a material is the high surface tension elastomer found in the film products from Gel-Pak, Incorporated. These materials have been tested to be satisfactory for direct contact with the semiconductor wafers and dies. The 180° reverse peel strength of these films is adjustable between 2 grams/25 mm and 42 grams/25 mm.

When a tacky layer is adhered to a surface and then peeled off, triboelectric charging can occur, leading to the possibility of a spark or electrostatic discharge (ESD). Small particles can be generated by ESD, so that it is desirable for the tacky surface to be sufficiently electrically conductive that triboelectrically generated currents can be dissipated before sufficient voltage is generated for ESD. There are both particulate and chemical additives that can be mixed with the tacky surface material or with the foundation material under the tacky surface to provide sufficient electrical conductivity.

Most surfaces that will be inspected by this invention will have roughness greater than the glassy surface specified for the tacky sheet. When the tacky sheet sticks to a relatively rough surface, it will conform to that surface and tend to mirror the roughness of that surface. Once the tacky sheet is peeled off of the surface to be inspected, it is highly desirable that the surface of the tacky sheet resumes its glassy state. A rough surface should only generate elastic deformations of the surface of the tacky sheet. Generally softer surfaces of the tacky sheet both make the surface higher tack and decrease the likelihood that a rough surface will make the sheet inelastically deform.

Bare silicon wafers are nearly ideal surfaces for optically detecting particles. One of the objectives in the design of the tacky sheet is that the sheet should resemble a bare silicon wafer as much as possible from a light scattering perspective. A wafer can be placed inside of a scanning tool optimized for looking at that wafer; the tacky sheet should be transportable onto the surface from which it is adhered to the optical scanner. Additional attributes of the surface of bare silicon wafer that make it ideal for inspection are surface roughness on the order of a few Angstroms, surface planarity of a few microns per centimeter, a high index of refraction for visible light, and a high absorption coefficient for visible light. The surface of the silicon wafer acts as a good mirror, meaning that illumination striking the surface is virtually all specularly reflected, as opposed to being scattered. Particles can be detected on the surface of a silicon wafer as a localized region from which light is scattered or is reflected with an anomalous phase shift.

The top surface of the tacky sheet is ideally specular or mirror-like. The surface roughness should be small enough that it generates little background optical scatter. Perturbation theory for light scatter from a nearly smooth surface with an rms roughness σ says that the total integrated scatter for illumination incident at a grazing angle $\theta_i$ is $16\pi^2\sigma^2 \cos^2(\theta_i)/\lambda^2$; see for example J. A. Ogilvy, *Theory of Wave Scattering From Random Rough Surfaces*, Higler, 1991, p.67. For a sensor detecting 0.3 micron latex spheres using 1:1 magnification, 14 micron pixels, 650 nanometer (nm) wavelength, and 80 degree angle of incidence, this corresponds to an rms roughness of less than approximately 10 nm.

The tacky surfaces produced by processes like Gel-Pak's tend to have sufficiently low short range rms roughness, however this is superimposed on a larger longer wavelength rippling. The length scale of the rippling is on the order of a millimeter. From a light scattering perspective this gentle rippling acts as a small variation in the angle of incidence, and is not a particular problem.

Surface illumination is partially transmitted into the tacky material, where it can scatter off of defects and particles in the bulk of the tacky layer and on the backing of the sheet. It is preferable that this transmitted light be absorbed by pigments or other optical absorbers in the tacky layer or in the backing sheet so as to suppress light scattering from buried or back side defects. If a transparent tacky layer is formed on a base cylinder, film, or disk, the surface of the base should be absorbing.

Particle detection techniques

Initial implementations of this invention will be designed to detect large particles. For visible and near infrared light wavelengths and typical particle index of refractions, large particles refer to particles larger than about 0.3 microns. As the process of making tacky sheet materials become better understood and controlled, small particle detection optics will be desirable.

Optical sensors for detecting large particles on surfaces typically use grazing angle illumination combined with forward scattering detection, as shown in FIG. 1. Illumination (6) is incident on the tacky sheet (4) surface at a range of angles close to $\theta_i$. $\theta_i$ should be at least 60 degrees with respect to the surface normal so that the light reflecting off of the surface of the tacky sheet (8) will be nearly 180 degrees phase shifted by the reflection. The interference of the incident (6) and reflected (8) fields will therefore be nearly destructive for heights from the surface that are small compared to $\lambda/4 \cos(\theta_i)$, which is useful in reducing scatter from roughness of the tacky surface. In the most preferred embodiment $75° < \theta_i < 89°$. The illumination (6) is preferably polarized perpendicular to the plane of incidence to minimize transmission into the tacky sheet (4). A particle (2) on the surface of the tacky sheet (4) whose mean circumference times the particles dielectric constant is greater than $\lambda$ will absorb and scatter the incident (6) and reflected (8) fields. The scattered illumination will generally not be isotropic, rather there will be lobes of low and high scattering intensity (10). The strongest of these lobes will generally be partially aligned with the direction of the reflected radiation (8); this is forward scattering. In the most preferred embodiment the detection optics (12) are oriented with an axial detection angle $\theta_0$ that is nearly aligned with the forward scatter direction. In the most preferred embodiment the reflected illumination (8) is obscured from entering the detection optics (12) by a light trap (14), stop, or mirror. Sensing the reflected illumination (8) at the detector (16) is not preferred because of the shot noise and variable baseline introduced by the reflected illumination. In the most preferred embodiment detection of the scattered light excludes the specular reflection of the illumination (8), but otherwise includes as much of the forward scattering solid angle (10) as possible.

Figure 2A:
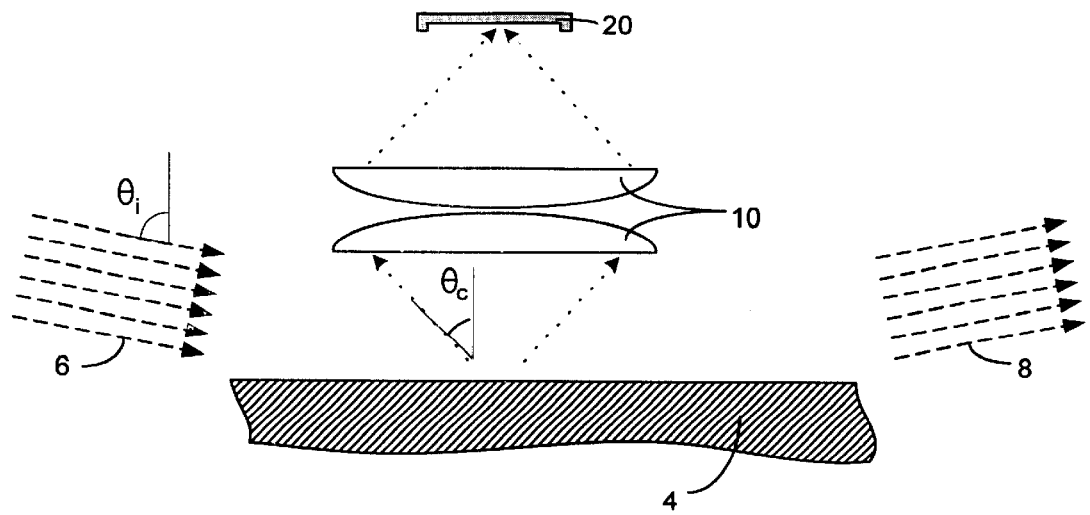
FIG. 2a shows light imaged normal to a surface using an aerial detector.
Figure 2B:
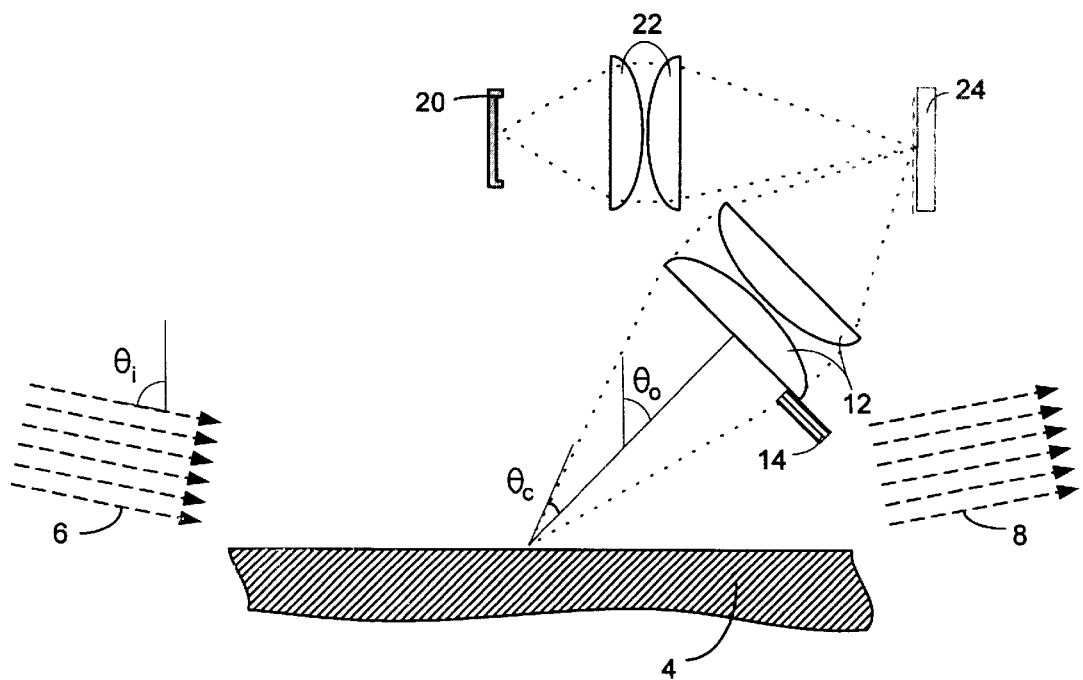
FIG. 2b shows light imaged away from the surface normal using an aerial detector.

There are several ways that the relative position of the light scattering particle or defect on the tacky surface can be determined. FIGS. 2a and b show preferred embodiments that utilize area imaging detectors (20) such as two dimensional CMOS or CCD arrays. In FIG. 2a the incident light (6) and the reflected light (8) both lie outside of the collection half angle $\theta_c$ of an objective (10) whose optical axis is nearly parallel to the normal to the tacky surface. Light scattered from the surface is imaged directly onto the imaging detector (20). In FIG. 2b the optical axis of the objective (10) is at an angle $\theta_o$ to the surface. The objective (10) images the tacky surface at unity magnification onto the surface of a grating or scattering surface (24), which is in turn imaged by relay lenses (22) onto the aerial detector (20). In both cases the detector produces an x-y coordinate within the imaged field for the position of a light scattering particle or defect.

Figure 3A:
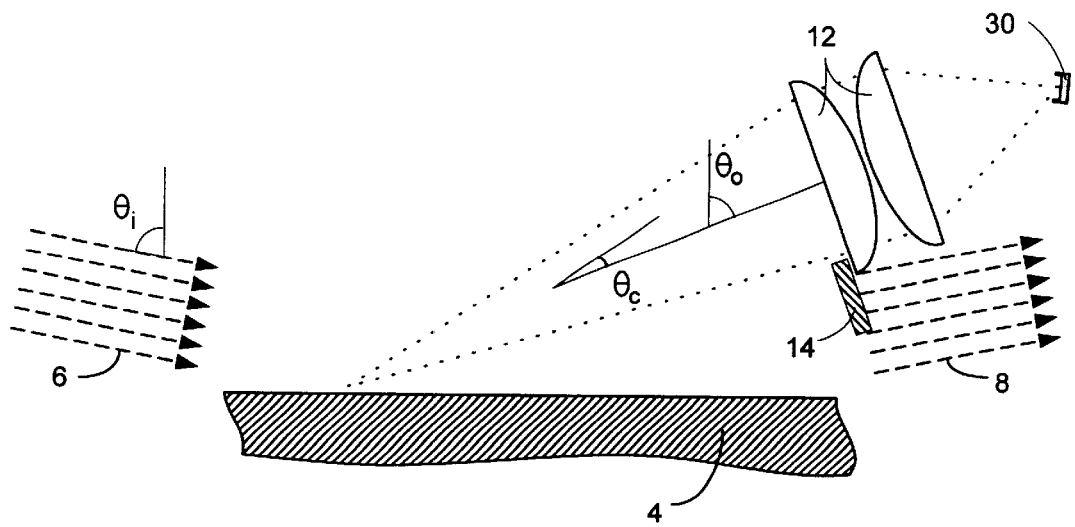
FIG. 3a shows light imaged away from the surface normal using a line detector.
Figure 3B:
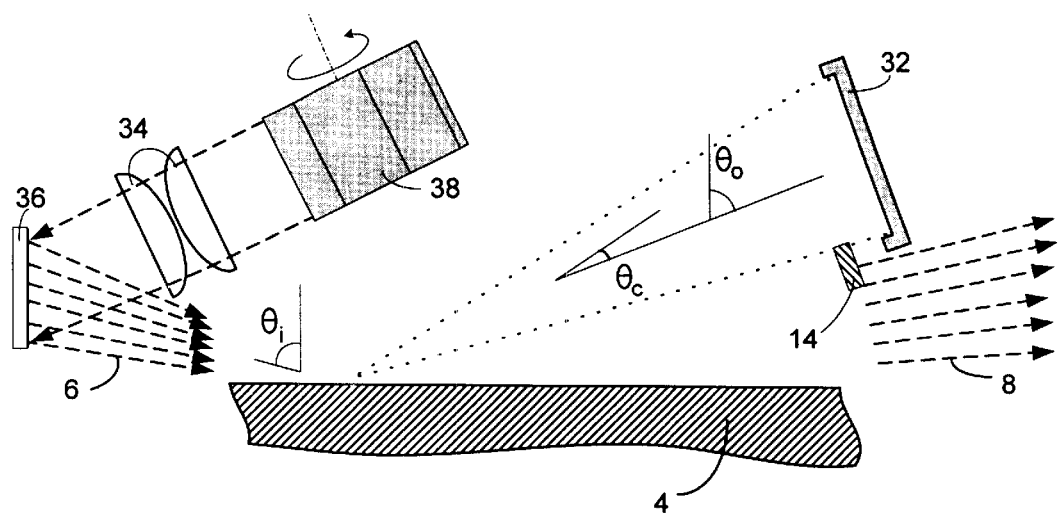
FIG. 3b shows light imaged away from the surface normal using a flying spot scanner.

In FIG. 3a the objective (12) images a line from the surface of the tacky sheet (4) onto a linear detector, such as a line CCD or CMOS detector. The linear detector provides the x coordinate of the particle or defect along the illuminated line. In FIG. 3b a rotating polygonal mirror (38) passes the illumination through a scan lens (34) and reflects the illumination from a planar mirror (36) to generate a flying spot illumination scan line on the surface of the tacky sheet (4). A broad area detector (32) such as a photodiode or photomultiplier tube records the scattered light intensity as a function of the rotational position of the polygon (38). The angular position of the polygonal mirror is linearly related to the x coordinate of the particle or defect along the scan line.

In the most preferred embodiment the optical resolution is significantly coarser than the size of a typical detected particle. For example the tacky surface of a roller two inches in circumference and one inch long is imaged in the most preferred embodiment with a linear array 2048 elements long. The rotary position of the roller is encoded to produce 11,400 timing pulses per rotation. This combination results in mapping the surface of the roller into about 23 million 14 microns×14 microns pixels. The optical resolution in this case is about 50 times coarser than the 0.3 micron particle sensitivity. This level of resolution adequately provides two functions. A 14×14 micron pixel is small enough that it does not provide significant background signal from surface roughness if the tacky sheet surface is as smooth as previously discussed. The tacky surface can be loaded with previously detected particles without significantly reducing the effective area of the roller. For example, if 10,000 single pixel particles are previously recorded on the roller, and a 7×7 pixel dead zone is applied around each of those particles where new light scattering events are ignored, then only 2 percent of the surface of the roller will be ignored in the next scan.

Increased sensitivity to small particles can be obtained by reducing the roughness and defect level of the tacky surface, shortening the illumination wavelength, increasing the collection solid angle, increasing the dwell time of the light sensor on a portion of the tacky surface, increasing the illumination intensity, reducing the imaged pixel size, reducing scatter and aberrations in the optics, and shrinking the size of the portion of the tacky surface imaged onto each detector. The tacky sheet technique is particularly suited to particle size amplification techniques such as described in U.S. Pat. No. 5,608,155.

Manipulating the tacky surface

Figure 4A:
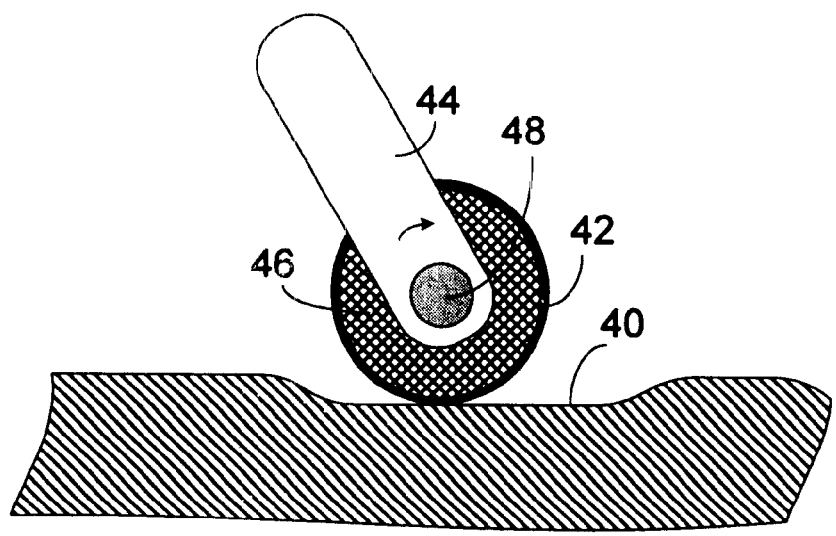
FIG. 4a shows a roller with a tacky sheet affixed to its cylindrical surface.

A simple mechanical method for simultaneously applying and removing the tacky sheet is to form the tacky sheet on the cylindrical exterior of a roller, as shown in FIG. 4a. The tacky sheet (42) rolls along the surface to be inspected (40) attached to a roller (46). The roller attaches to the frame of the inspection apparatus (44) through a bearing (48). The roller can be driven by a motor or by the action of the user of the apparatus. In less preferred embodiments the roller can have the surface of a frustum, an ellipsoid, and a hyperboloid.

Figure 4B:
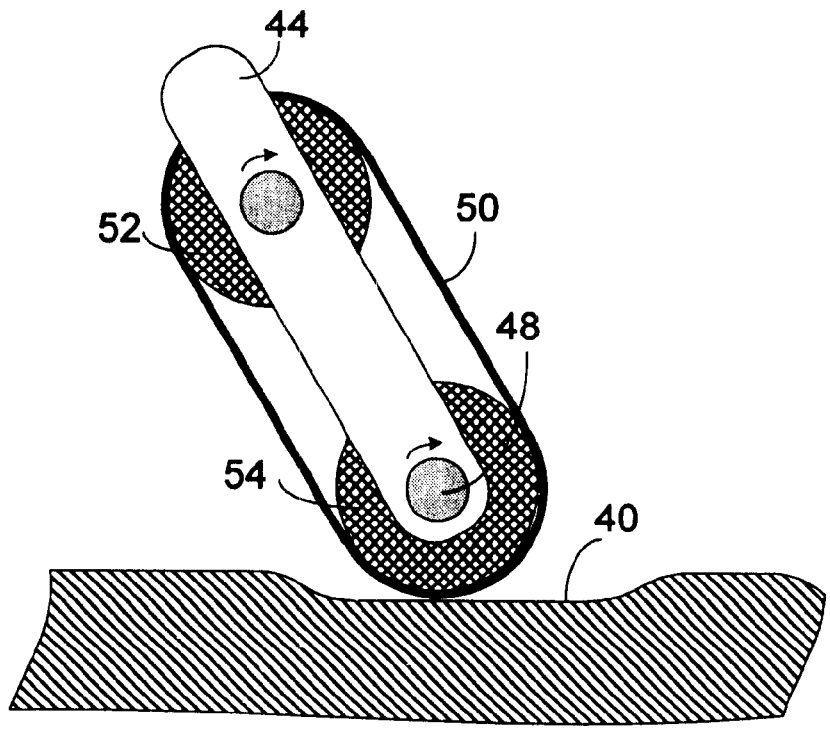
FIG. 4b shows a roller pair with a continuous tacky sheet.

A longer tacky sheet can be accommodated with a two roller implementation, as shown in FIG. 4b. The tacky sheet

(50) is in the form of a belt. The tacky sheet (50) passes over two rollers. Roller (54) applies and removes the tacky sheet (50) from the surface to be inspected (40), and roller (52) maintains tension on the tacky sheet (50). This implementation would provide greater surface area than a single roller for applications where small diameter rollers are required.

Figure 4C:
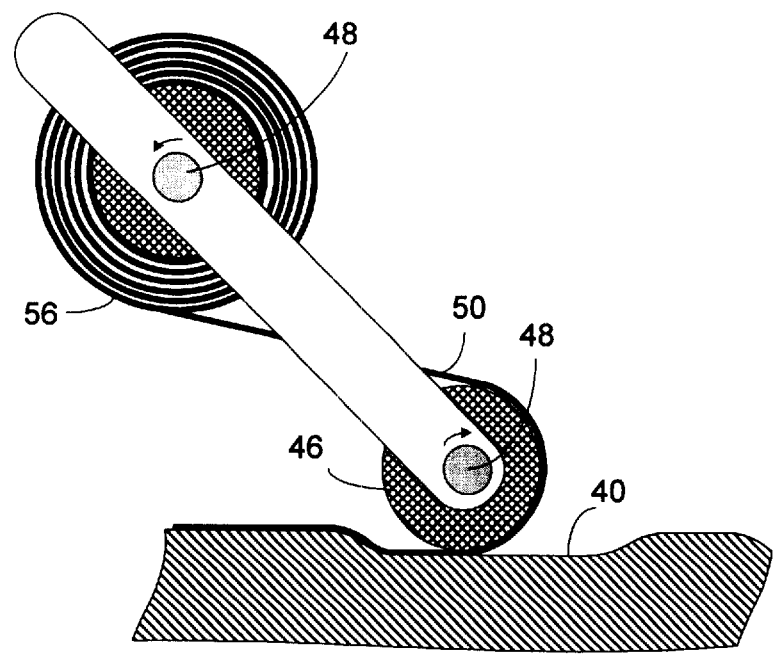
FIG. 4c shows a tacky sheet spool with an application roller.

FIG. 4c shows a tacky sheet applicator similar in operation to a window shade. A spool of tacky sheet material (56) is payed out over a roller (46) onto the surface to be inspected (40). Once the surface has had tacky sheet applied to it, the process is reversed. The roller (46) removes the tacky sheet from the surface (40) and the tacky sheet is again wound up on the spool (56).

Figure 4D:
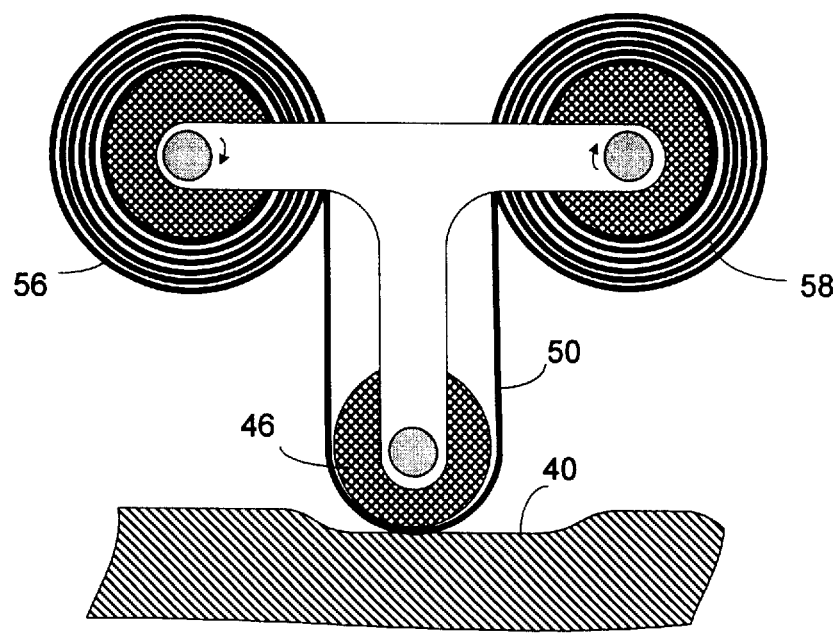
FIG. 4d shows a tacky sheet supply and take up spool with an application roller.

FIG. 4d shows a tacky sheet applicator in which a spool of tacky sheet material (56) is payed out over a roller (46) while being wound up on a take up spool (58). This implementation has the advantage that the tacky surface will typically be adhered to a surface just once, so that the contamination from that surface is captured and archived on the tacky sheet as it is wound on the take up spool.

Figure 4E:
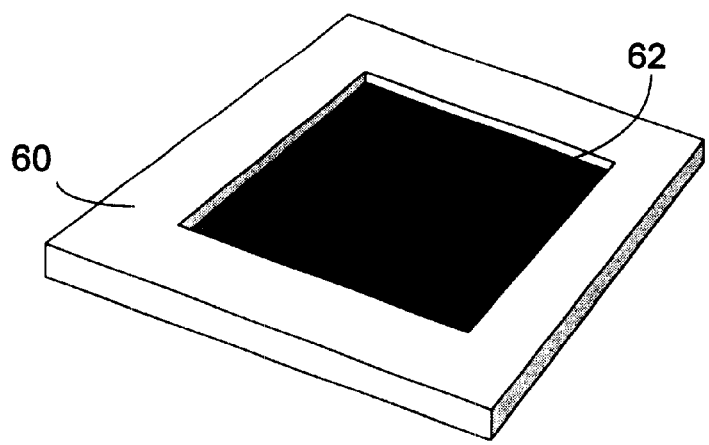
FIG. 4e shows a tacky sheet mounted in a frame.

FIG. 4d shows a planar tacky sheet (62) captured in a frame (60) in a manner similar to a 35 mm slide. This configuration of tacky sheet is useful for inspecting complex objects, such as the head disk armature (64) shown in FIG. 4e. The frame (60) and tacky sheet (62) can be slipped between features of the object (64) to inspect the surface (66). The tacky sheet (62) is adhered by proximity to the surface, by a roller or stylus (68) pressing on the back of the tacky sheet, or by the operator's finger pressing on the back of the tacky sheet. The tacky sheet (62) is removed from the surface (66) by lifting the frame (60) away from the surface (66).

Figure 4F:
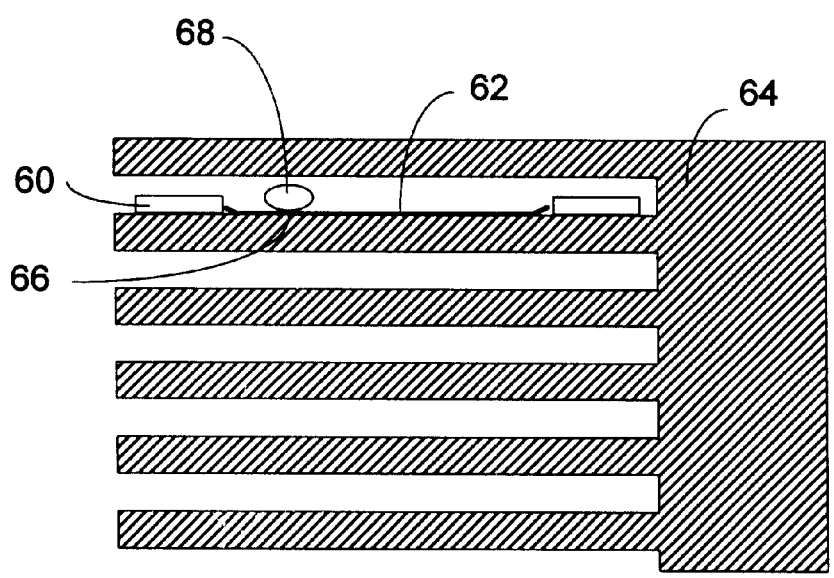
FIG. 4f shows the tacky sheet of FIG. 4e applied to a hidden surface of a part.

The optical techniques described for inspecting for particulate contamination inspection view the side of the tacky sheet to which the particles are attached. This requires that the tacky sheet be moved or re-positioned from being adhered to the surface to be inspected to being positioned proximate to the optical inspection apparatus. In the less preferred geometries such as that shown in FIGS. 4e and 4f, a discrete portion of the tacky sheet can be placed under a static aerial inspection apparatus such as is shown in FIGS. 2a and b. In the more preferred line scan geometry of FIGS. 3 and 4 the tacky sheet is moved continuously with respect to the optical detector. In these more preferred embodiments the apparatus manipulating the position of the tacky surface must supply the instantaneous precise position of the tacky surface to the optical detector.

FIG. 5a shows the most preferred embodiment for the mechanism manipulating the position of the tacky sheet with respect to the optical detector to supply the instantaneous precise position of the tacky surface to the optical detector. The tacky sheet (42) is on the cylindrical surface of a roller (46). The roller (46) is clamped to a tapered bushing (78) by a knurled nut (80). The tapered bushing (78) is held by a set screw on the output shaft (76) of a gear head (72), and the gear head (72) is in turn driven by a double shafted motor (70). A rotary encoder (74) measures the instantaneous rotary position of the motor (70). MicroMo Inc. manufactures an example of this combination of motor, encoder, and gear head. The gear head (72) attaches to the stationary frame (44) of the apparatus. A bearing (48) supports one end of the roller (46) with sufficient clearance so that an operator can replace the roller (48) by removing the knurled nut (80).

Figure 5B:
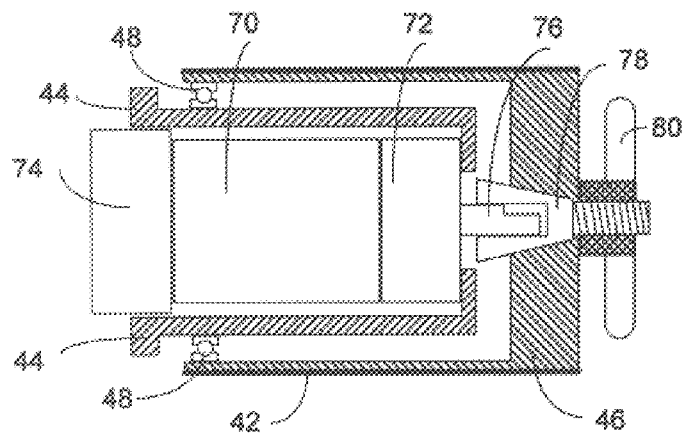
FIG. 5b shows a roller with a tacky surface and a predetermined array of asperities.
Figure 5B:
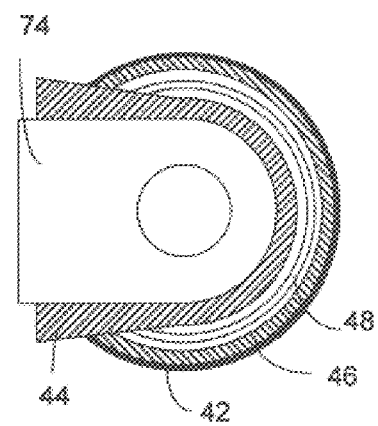
Figure 5B:
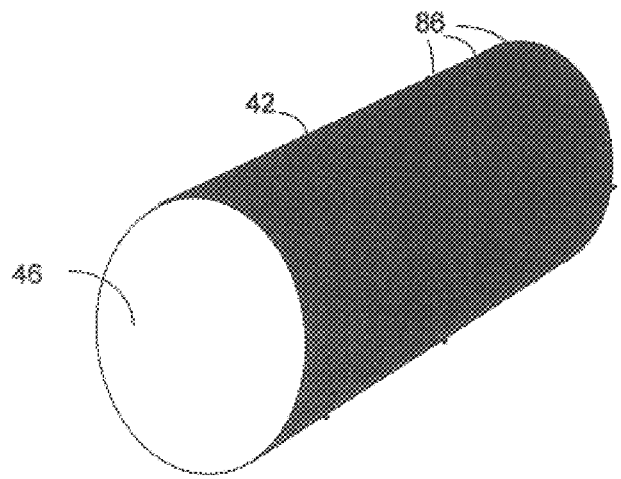

FIG. 5b shows a preferred embodiment to supply the instantaneous precise position of the tacky surface to the optical detector. A predetermined regular array of asperities, particles, or defects (86) is manufactured to be present on the tacky sheet (42). The optical detector detects these features (86) along with additional particulate contamination acquired from the surface to be inspected. A relatively crude instantaneous measure of the position of the tacky surface with respect to the optical detector, such as timestamping events or counting scan lines, can be correlated to the predetermined positions of the features (86) to interpolate the positions of the additional particulate contamination acquired from the surface to be inspected.

In an additional preferred embodiment the initial random particulates and defects on the tacky sheet are dense enough that they provide good alignment accuracy while not being so dense as to significantly cover the surface of the tacky sheet or burden the controller with extraneous calculations. These random defects and particulates are used to supply the instantaneous precise position of the tacky surface with respect to the optical detector.

Figure 5C:
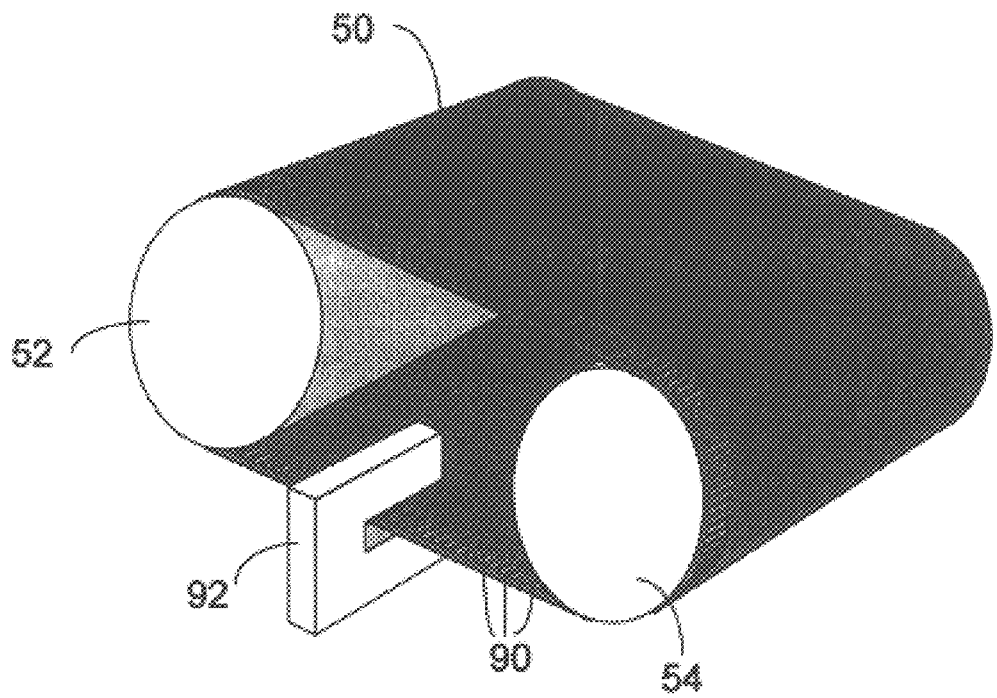
FIG. 5c shows a tacky sheet with an edge mounted detector.

FIG. 5c shows a preferred embodiment to supply the instantaneous precise position of the tacky surface to the optical detector. The tacky sheet (50) is marked with a regular array of indicators (90) whose passage is sensed by a detector (90). The indicators (90) can be relatively reflective or transparent regions for an optical detector (90). The indicators (90) can be relatively high dielectric regions for a capacitive detector (90). The indicators (90) can be perforations in the tacky sheet (50) that mesh with gear sprockets in a mechanical detector (90).

Figure 5D:
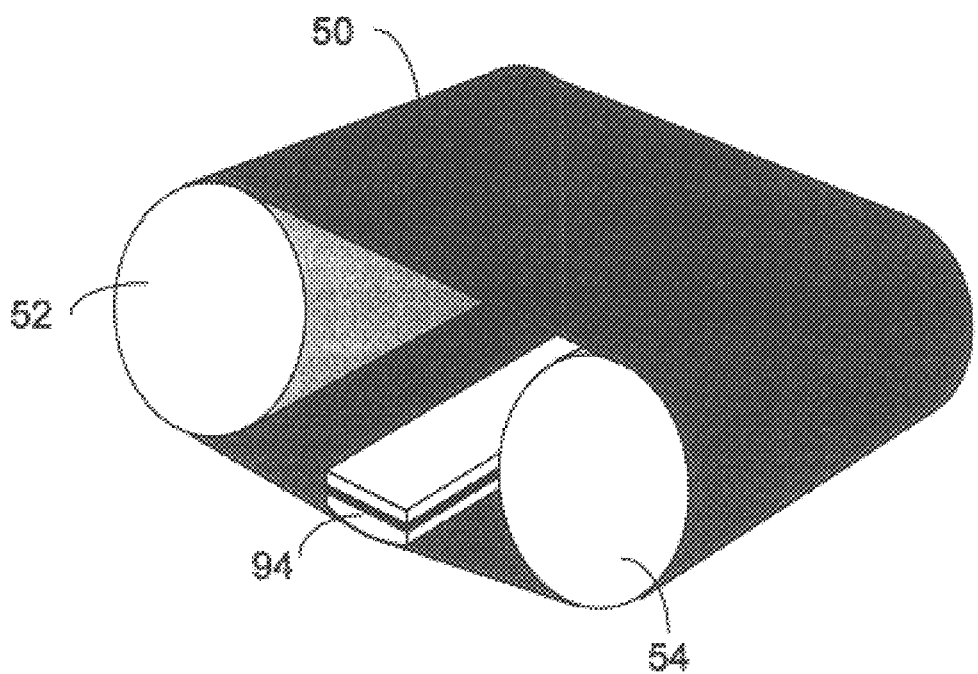
FIG. 5d shows a tacky sheet with a magnetic read/write head.

FIG. 5d shows a preferred embodiment to supply the instantaneous precise position of the tacky surface to the optical detector. The tacky sheet (50) is backed with a magnetic media such as is found on magnetic tape. A magnetic head (94) can read and write magnetic information in the magnetic media on the tacky sheet (50). The tacky sheet (50) is manufactured with formatted magnetic information written in the magnetic media on the tacky sheet (50), so that the magnetic head (94) can recognize the relative position of the tacky sheet (50) as the tacky sheet (50) passes by the magnetic head (94). The configuration of FIG. 5d is of particular interest in that information resulting from the inspection of the tacky sheet can be added by the magnetic head (94) to the formatted magnetic information, causing the tacky sheet (50) to act as a magnetic information storage medium.

Controller

Typically an operator of the apparatus is interested in an average particle density on the surface being inspected. A minimal function for a controller in this apparatus is to divide the number of detected particles by the area of the surface being inspected. A controller must also interact with the operator to display information, respond to switches and actuators, and monitor the operation of the apparatus.

Figure 6:
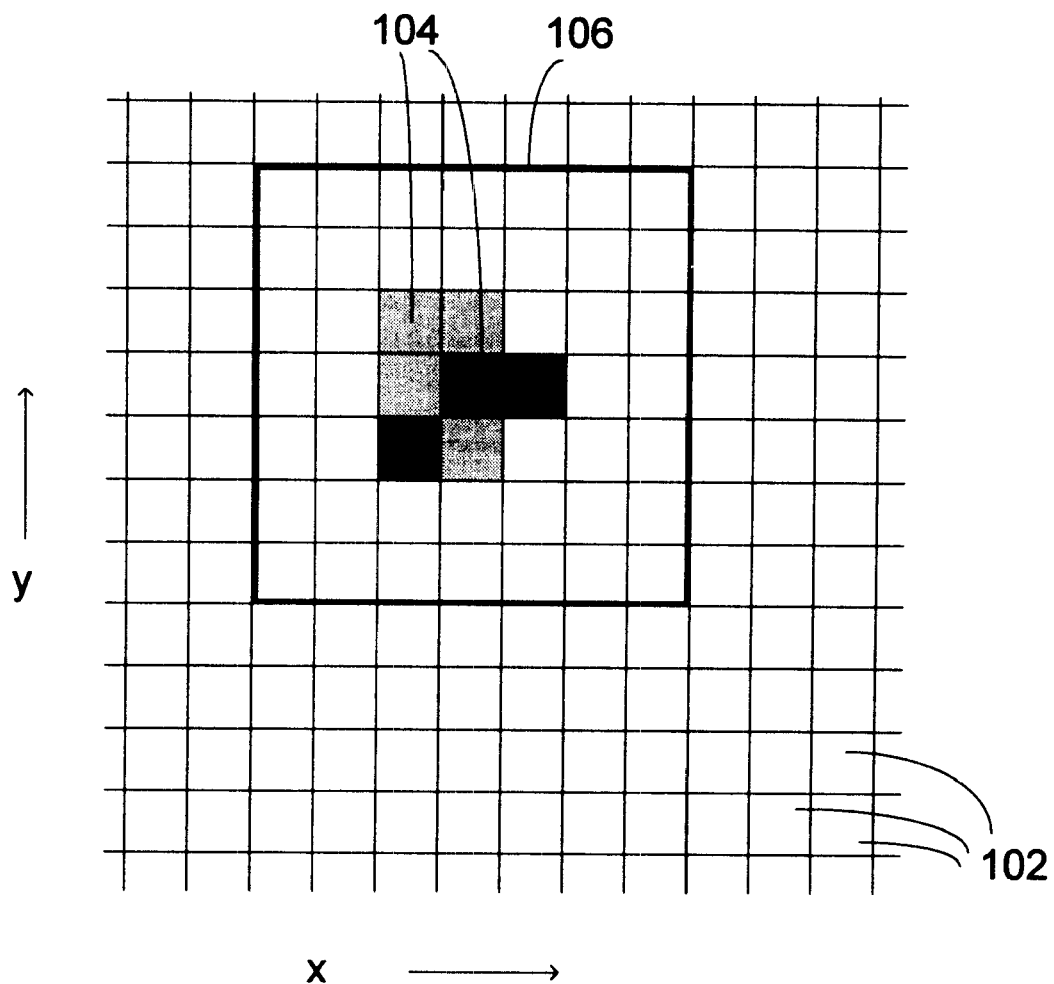
FIG. 6 shows an array of pixels with a superimposed particle signal.

In the most preferred embodiment the controller performs an additional function to reduce the number of detected light scattering events to a minimum likely number of particles. FIG. 6 demonstrates this process. When an image is broken up into pixels (102), it is likely that even a true point source will be imaged close enough to the boundary between two or more pixels that light scattering intensity is recorded in several neighboring pixels. Other effects can cause the number of pixels registering significant light scattering to be even greater; these effects include defocus, optical aberrations, and spatially extended particles. In FIG. 6 there are seven pixels (104) that record significant light scatter intensities from a single particle. The controller sorts through the recorded pixel data to group these seven pixels (104) as a single event; in this case the seven pixels are considered an isolated particle because there is a two pixel wide band around the seven pixels that contains no significant light scatter. The controller merges together the addresses and detected scattering intensities of the seven pixels (104) to a much smaller data set comprising two opposite corner locations of the bounding box (106) and the integrated intensity of the seven pixels. In alternative preferred embodiments the controller can apply different criteria for associating pixels together, such as nearest neighbors, next nearest neighbors, expand followed by shrink, and other techniques well known to those skilled in the art of image processing. In alternative preferred embodiments the controller can merge the variable number of clustered pixels associated with a single particle into different output data sets, including centroids, more complicated perimeters, tree structures, link lists, and heaps.

Figure 7:
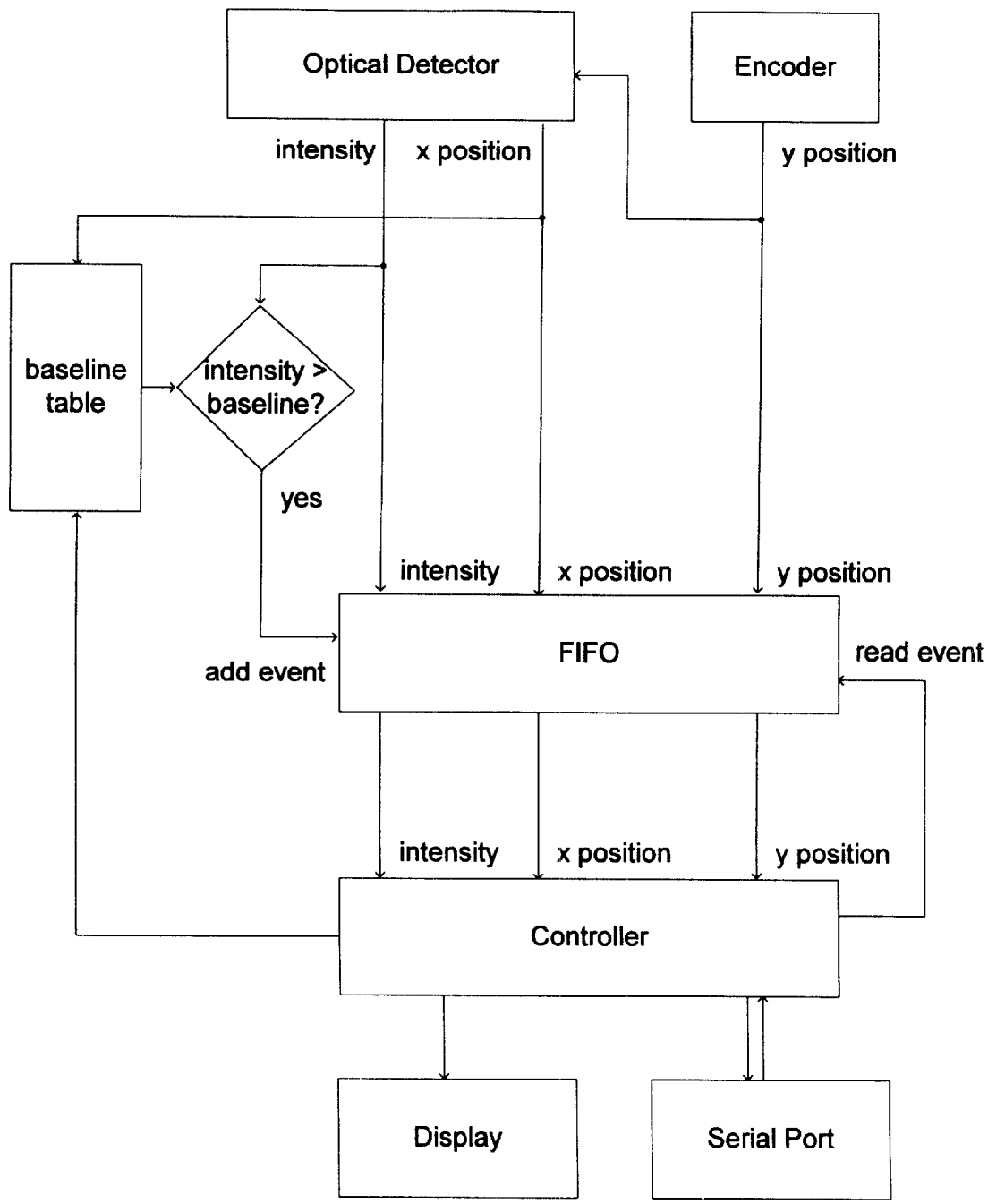
FIG. 7 shows data flow for processing the signal from the optical detector.

In the most preferred embodiment the function of identifying pixels associated with significant levels of light scattering is handled in a dedicated hardware controller separate from the software driven controller. FIG. 7 shows more detail of the data flow in a dedicated hardware controller. The optical detector produces a sequence of light scattering pixel intensities as a function of each pixel's x position. An encoder which supplies the precise position of the tacky sheet produces the pixel's y positions as well as indicating to the optical detector when a new x scan line should start. The light scattering intensities are compared against a stored baseline as a function of the pixel's x position. If the detected scattering intensity is greater than the baseline, the pixel's x location, the pixel's y location, and the pixel's light scattering intensity are stored in a first in first out memory. In the case of an area scanning detector, the detector produces both the pixel's x and y locations. In a less preferred embodiment the baseline can be made independent of pixel's x location, and it can be made dependent on both the pixel's x and y location.

Figure 8:
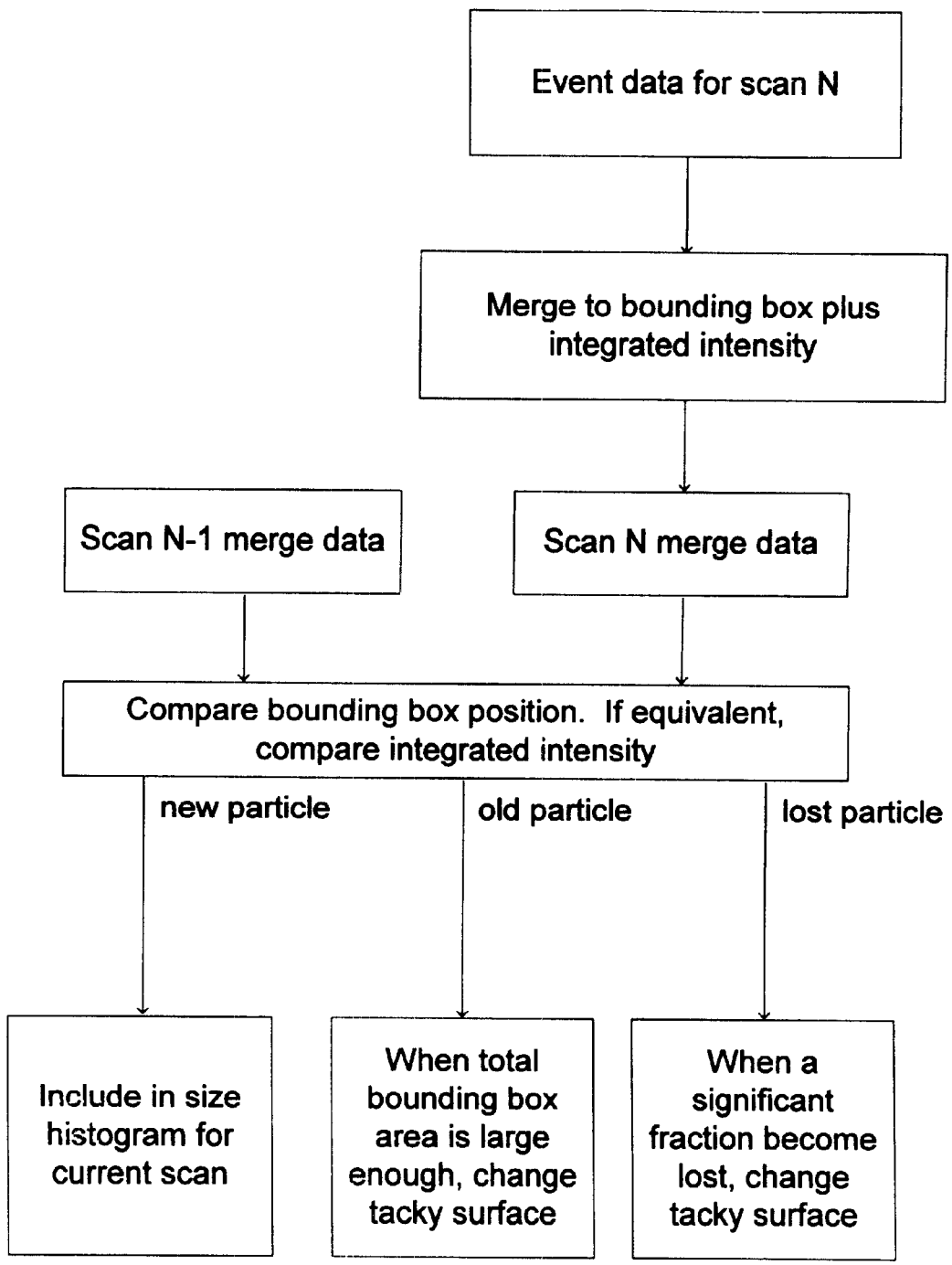
FIG. 8 shows data flow for comparing signals from two sequential inspections of the tacky sheet.

FIG. 8 shows data flow that occurs in a software driven controller associated with the dedicated hardware controller shown in FIG. 7. Event data for the current scan or scan N is read in from the first in first out memory and merged into single particle events, as described in FIG. 6. The merged data for the current scan is compared to the merged data from the previous scan or scan N-1. If an event in scan N cannot be associated with any event in scan N-1 within the positioning accuracy of the tacky sheet manipulator, that event from scan N is taken to be a new particle added to the tacky sheet from the surface under inspection. If an event from scan N-1 cannot be associated with any event in scan N within the positioning accuracy of the tacky sheet manipulator, that event from scan N-1 is taken to be a particle that somehow has been removed from the tacky sheet. When the number of particles removed from the tacky sheet gets above a threshold, the tacky sheet has lost its tackiness and needs to be replaced. If an event from scan N is associated with an event from scan N-1, the event is taken to be a particle resident on the tacky sheet. When the cumulative area of the tacky sheet associated with such resident particles gets above a threshold, the tacky sheet is filled up and needs to be replaced. The threshold for the tolerable number of resident particles is in part determined by the processing time needed to merge and compare the thousands of resident particles within the few seconds required for a tacky sheet to cycle passed the optical detector.

Preferred embodiments

Figure 9A:
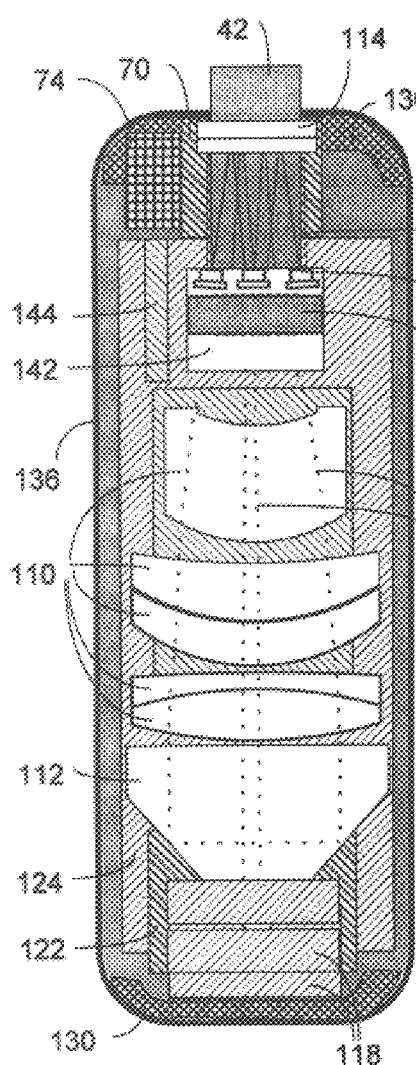
FIGS. 9a, b, and c shows a preferred embodiment of the apparatus utilizing two pass optics.
Figure 9B:
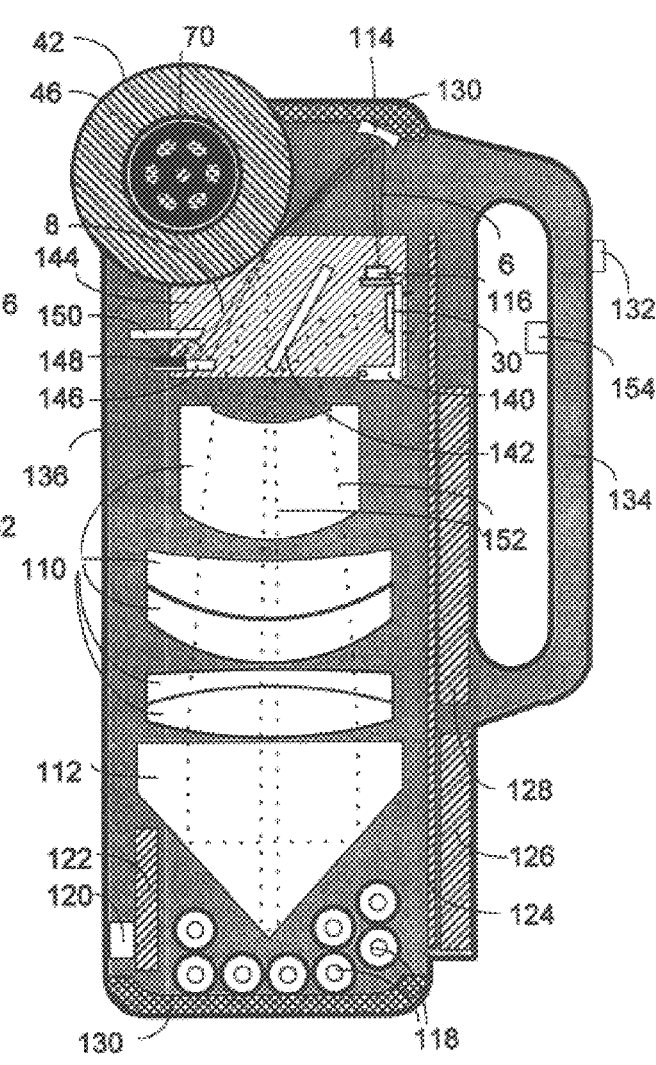
Figure 9C:
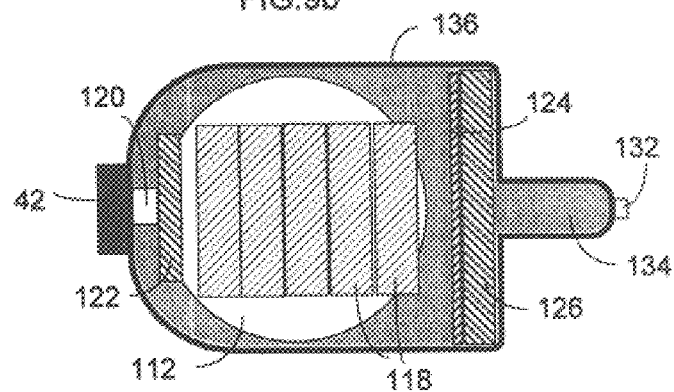

FIGS. 9a, b, and c show three views of the most preferred embodiment of the apparatus. A roller (46) whose cylindrical surface is coated with a tacky sheet (42) is removably attached to motor and gear head (70). The rotation of the roller is monitored by an optical encoder (74). A scan line on the tacky sheet is illuminated by three solid state lasers (116), whose output (6) is reflected and focussed by a cylindrical mirror (114). The specular reflection (8) off of the tacky sheet (42) is reflected by a mirror (146) onto a neutral density filter (150). A fraction of the illumination striking the neutral density filter (150) reflects onto a position sensing diode (148), which produces an output related to the instantaneous radial distance between the axis of the motor (70) and the surface of the tacky sheet (42). The combination of the mirror and the neutral density filter acts as a light trap for the specularly reflected illumination (8). One half of the entrance aperture of the collimating lens (110) collects scattered light (152) from particulates or defects. A Nikon 105 mm f1.8 lens for a 35 mm camera performs acceptably as the collimating lens (110). A corner cube (112) aligned with the axis of the collimating lens (110) returns the scattered light through the collimating lens to exit from the opposite half of the entrance aperture of the collimating lens (110). A planar mirror (142) reflects the scattered light exiting from the collimating lens onto a CCD line scan detector (30), such as a Sony ILX503A. Since the numerical aperture of this unity magnification optical system is about 0.25 both at the tacky sheet and at the detector, the depth of focus of the image at the detector is about 12 microns, so that autofocus of the detector position may be required. The detector is mounted on a pivoting bracket (140) that is servoed with a voice coil to track the output from the position sensing diode (148). The output signals from the detector (30) is processed by electronic components on the main circuit board (124), and further processed by an embedded microcomputer (128). The output information is displayed on a backlit liquid crystal display (126) and is communicated by an infrared serial port (120 and 124) to an external computer. Rechargeable batteries (118) supply power to the apparatus. The motor (70) and lasers (116) are controlled by components on an ancillary circuit board (144). The case (138) contains foam inserts (130) at the ends to minimize the impact shock should the apparatus be dropped accidentally. An operator manipulates the apparatus with a handle (134), a scan active push button (132), and a scanning push button (154). A removable cover (not shown) protects the roller from contamination when the apparatus is not in use.

Figure 10:
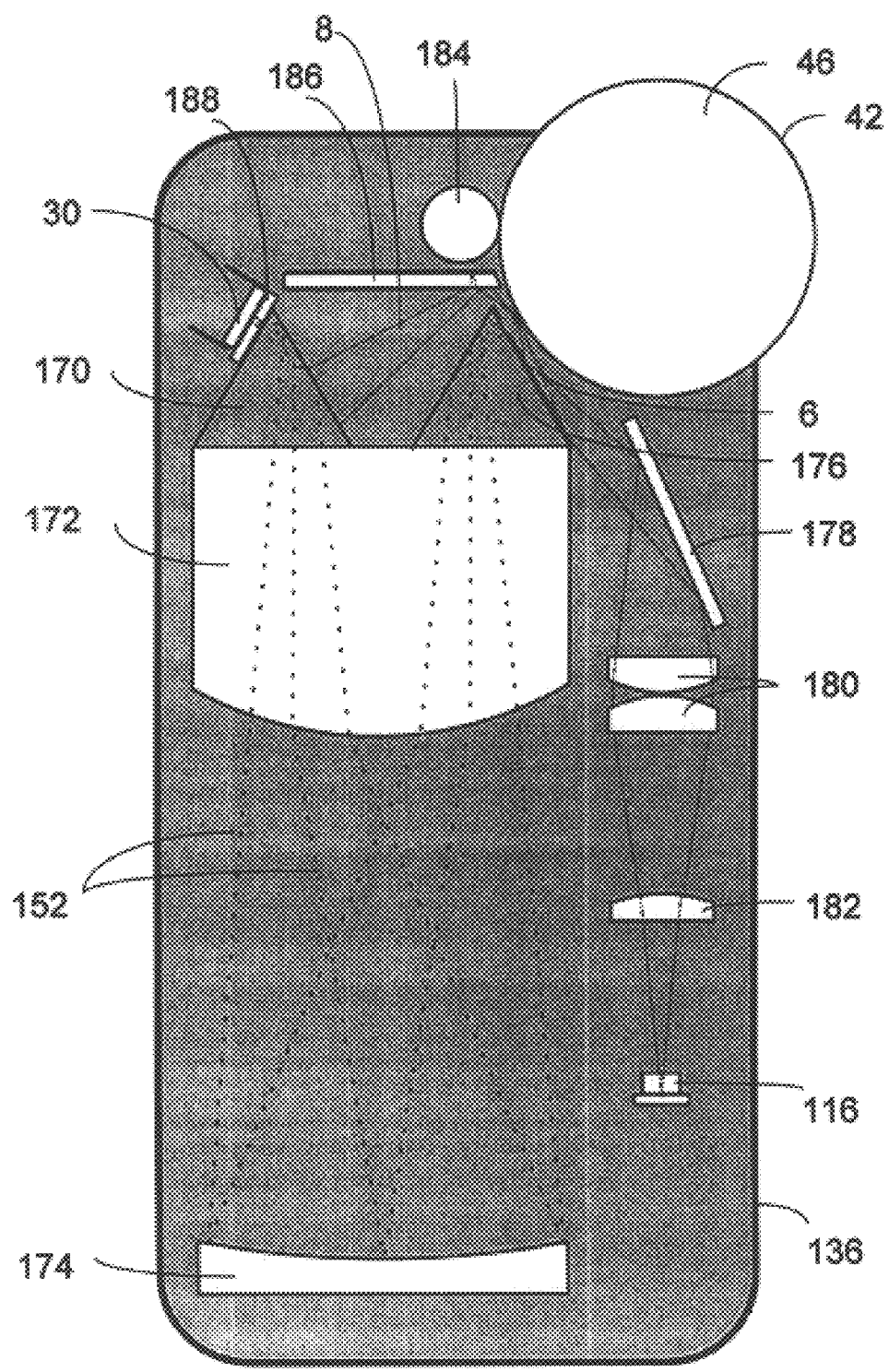
FIG. 10 shows an embodiment of the apparatus utilizing Dyson optics.

FIG. 10 shows an additional preferred embodiment of the apparatus. A roller (46) has a tacky sheet (42) affixed to its cylindrical surface. Illumination (6) from a laser diode (116) passes through a cylindrical lens (182) and a collimator lens (180), where it is reflected by a planar mirror (178) and a mirrored surface of a glass prism (176) onto the tacky surface (42). The reflected illumination (8) is absorbed in a light trapped formed by a mirror (186) and blackened surfaces on the glass prisms (176) and (170). Scattered light from particles and defects (152) is collected by a non-mirrored portion of the glass prism (176) and is reflected through a Dyson unity magnification lens and mirror combination (172) and (174). The image of the scattered light is formed on a line scanner (30) through a spacer (188). A rotatable pin (188) holds the position of the tacky surface constant with respect to the Dyson optics.

A presently preferred embodiment of the present invention and many of its improvements have been described with a degree of particularity. It should be understood that this description has been made by way of preferred example, and that the invention is defined by the scope of the following claims.

Although the present invention has been described with reference to preferred embodiments, workers skilled in the art will recognize that changes may be made in form and detail without departing from the spirit and scope of the invention.

What is claimed is:

1. An apparatus using a tacky sheet for detecting particulate contamination on a surface, comprising:
    an applicator means which adheres a portion of the tacky sheet to the surface;
    a removal means which peels the portion of the tacky sheet from the surface;
    an optical detector which inspects the portion of the tacky sheet to produce scattering location data, whereby the scattering location data corresponds to locations of defects and particulate contamination on the portion of the tacky sheet; and
    a control means, the control means acquiring first scattering location data from the portion of the tacky sheet prior to adhering the portion of the tacky sheet to the surface, the control means acquiring second scattering location data from the portion of the tacky sheet after adhering the portion of the tacky sheet to the surface, the control means subtracting first scattering location data from corresponding second scattering location data to make third scattering location data whereby third scattering location data corresponds to locations of particulate contamination transferred to the tacky sheet from the surface.

2. The apparatus of claim 1, wherein the optical detector comprises a flying spot scanner.

3. An apparatus using a tacky sheet for detecting particulate contamination on a surface, comprising:
    a first optical detector which inspects a portion of the tacky sheet, the optical detector producing first scattering location data corresponding to defect and particulate locations on the portion of the tacky sheet;
    an applicator means which adheres the portion of the tacky sheet to the surface;
    a removal means which peels the portion of the tacky sheet from the surface;
    a second optical detector which inspects the portion of the tacky sheet, the optical detector producing second scattering location data corresponding to defect and particulate locations on the portion of the tacky sheet; and
    a control means which subtracts the first scattering location data from the corresponding second scattering location data producing third scattering location data, whereby third scattering location data corresponds to locations of particulate contamination transferred to the tacky sheet from the surface.

4. The apparatus of claims 3, 1 or 2, wherein the optical detector utilizes grazing angle illumination.

5. The apparatus of claim 3, wherein the tacky sheet moves with respect to the optical detector, further comprising:
    a line scan sensor producing scattering location data perpendicular to the direction of travel of the tacky sheet with respect to the optical detector; and
    a motion encoder producing scattering location data parallel to the direction of travel of the tacky sheet with respect to the optical detector.

6. The apparatus of claim 5, wherein the tacky sheet is dispensed from a spool.

7. The apparatus of claim 3, further comprising a roller whose cylindrical surface is affixed to the tacky sheet, the roller being the applicator means for adhering the tacky sheet to the surface, and the roller being the removal means for peeling the tacky sheet from the surface.

8. The apparatus of claim 3, wherein the control means computes the aerial particle density of the third scattering location data.

9. A process for detecting particulate contamination on a surface, comprising:
    inspecting a portion of a tacky sheet with an optical detector, the optical detector producing first scattering location data corresponding to the locations of defects and particulates on the portion of the tacky sheet;
    adhering the portion of the tacky sheet to the surface;
    removing the portion of the tacky sheet from the surface;
    inspecting the portion of the tacky sheet with an optical detector, the optical detector producing second scattering location data corresponding to the locations of defects and particulates on the portion of the tacky sheet; and
    subtracting the first scattering location data from the corresponding second scattering location data producing third scattering location data, whereby the third scattering location data corresponds to the locations of particulate contamination transferred to the portion of the tacky sheet from the surface.

10. The processes of claim 9, wherein the tacky sheet is adhered to the surface with a roller, and the tacky sheet is removed from the surface with the same roller.

11. The process of claim 9, wherein the optical detector utilizes grazing angle illumination.

12. The process of claim 9, wherein the tacky sheet is optically absorbing.

13. A process for detecting particulate contamination on a surface, comprising:
    inspecting a portion of a tacky sheet with an optical detector, the optical detector producing first scattering location data corresponding to the locations of defects and particulates on the portion of the tacky sheet;
    adhering the portion of the tacky sheet to a first portion of the surface;
    removing the portion of the tacky sheet from the first portion of the surface;
    inspecting the portion of the tacky sheet with an optical detector, the optical detector producing second scattering location data corresponding to the locations of defects and particulates on the portion of the tacky sheet;
    subtracting the first scattering location data from the corresponding second scattering location data producing third scattering location data, whereby the third scattering location data corresponds to the locations of particulate contamination transferred to the portion of the tacky sheet from the first portion of the surface;
    adhering the portion of the tacky sheet to a second potion of the surface;
    removing the portion of the tacky sheet from the first portion of the surface;
    inspecting the portion of the tacky sheet with an optical detector, the optical detector producing fourth scattering location data corresponding to the locations of defects and particulates on the portion of the tacky sheet; and
    subtracting the second scattering location data from the corresponding fourth scattering location data producing fifth scattering location data, whereby the fifth scattering location data corresponds to the locations of particulate contamination transferred to the portion of the tacky sheet from the second portion of the surface.

14. A process for detecting particulate contamination on a surface, comprising:

adhering a portion of a tacky sheet to the surface, the tacky sheet having a predetermined number of locations of particulate contamination;

removing the portion of the tacky sheet from the surface;

inspecting the portion of the tacky sheet with an optical detector to produce a measured number of locations of particulate contamination; and subtracting the predetermined number of locations of particulate contamination from the measured number of locations of particulate contamination.

* * * * *